United States Patent [19]

Labeda et al.

[11] Patent Number: 4,608,343

[45] Date of Patent: Aug. 26, 1986

[54] BIOLOGICALLY PORE CULTURE OF STREPTOMYCES MAJORCIENSIS LABEDA

[75] Inventors: David P. Labeda, Monsey; Joseph J. Goodman, Spring Valley; Donald B. Borders, Suffern, all of N.Y.; Raymond T. Testa, Cedar Grove, N.J.; John H. E. J. Martin, deceased, late of New City, N.Y., by Mary B. Martin, executrix

[73] Assignee: American Cyanamid Company, Stamford, Conn.

[21] Appl. No.: 739,334

[22] Filed: May 30, 1985

Related U.S. Application Data

[62] Division of Ser. No. 507,184, Jun. 23, 1983.

[51] Int. Cl.$^4$ .................. C12P 21/00; C12P 13/00; C12P 1/06

[52] U.S. Cl. ................... 435/253; 435/68; 435/128; 435/169

[58] Field of Search ............... 435/253, 169, 886, 68, 435/128

*Primary Examiner*—Thomas G. Wiseman
*Assistant Examiner*—Rebecca L. Thompson
*Attorney, Agent, or Firm*—Susan H. Rauch

[57] ABSTRACT

This disclosure describes four new antibacterial agents designated LL-C08078$\alpha_1$, LL-C08078$\alpha_2$, LL-C08078$\alpha_3$ and LL-C08078$\beta$ produced in a microbiological fermentation under controlled conditions using a new strain of a new species of the genus Streptomyces called *Streptomyces majorciensis* Labeda, sp. nov., and mutants thereof. These new antibacterial agents are active against a variety of microorganisms and thus are useful in inhibiting the growth of such bacteria wherever they may be found. In addition, these agents are active as growth promotants in warm-blooded animals.

3 Claims, 14 Drawing Figures

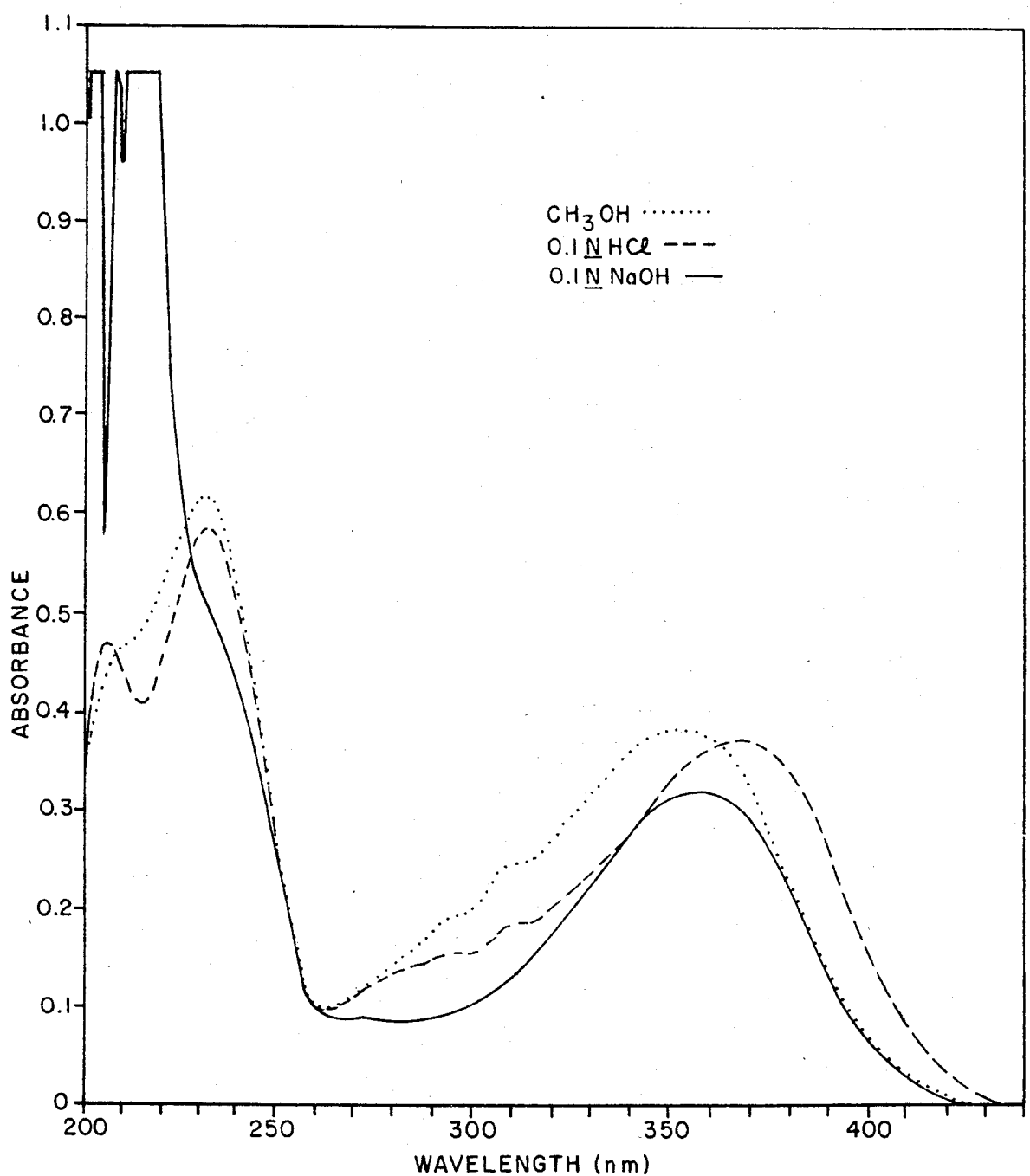
FIGURE I

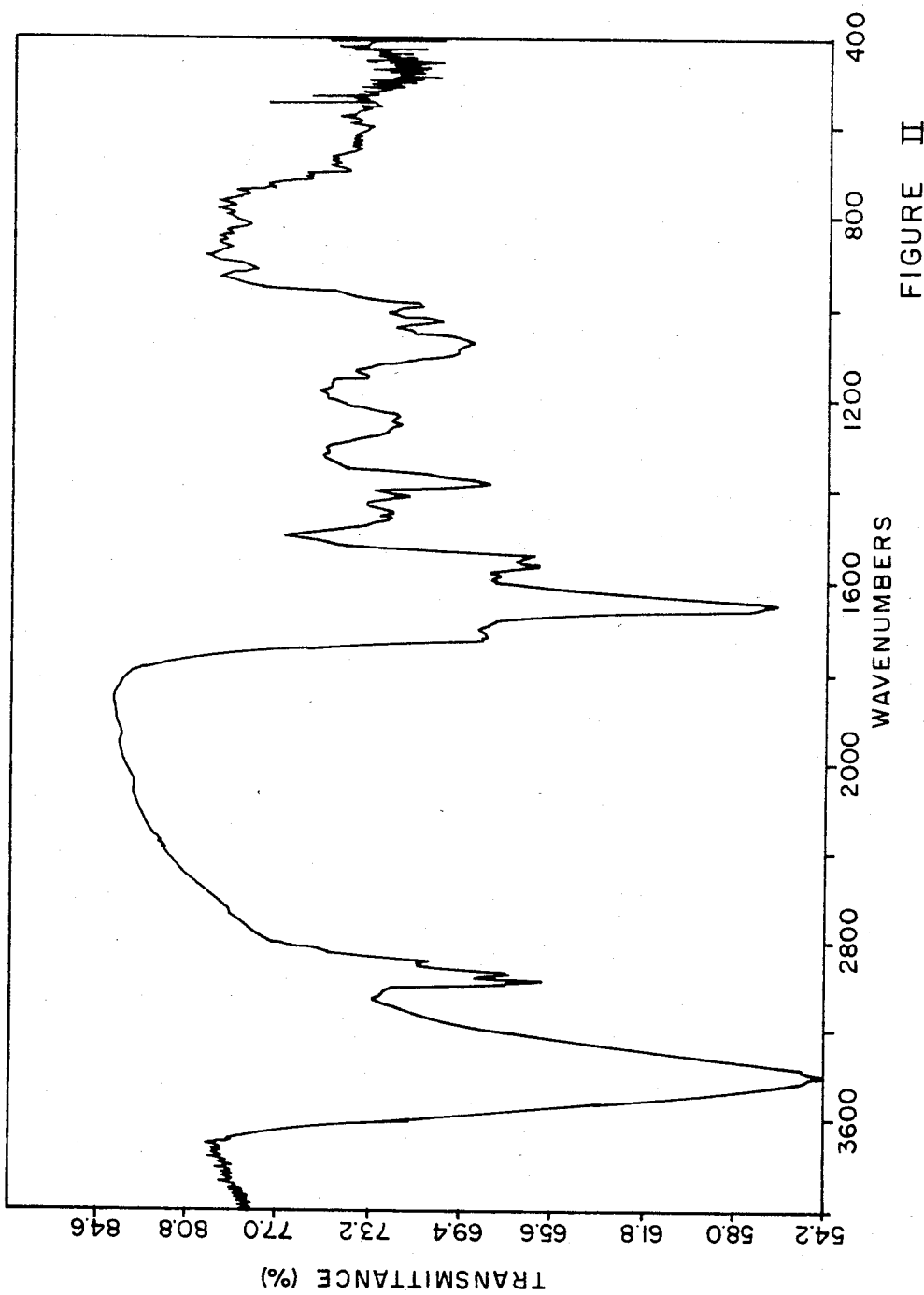

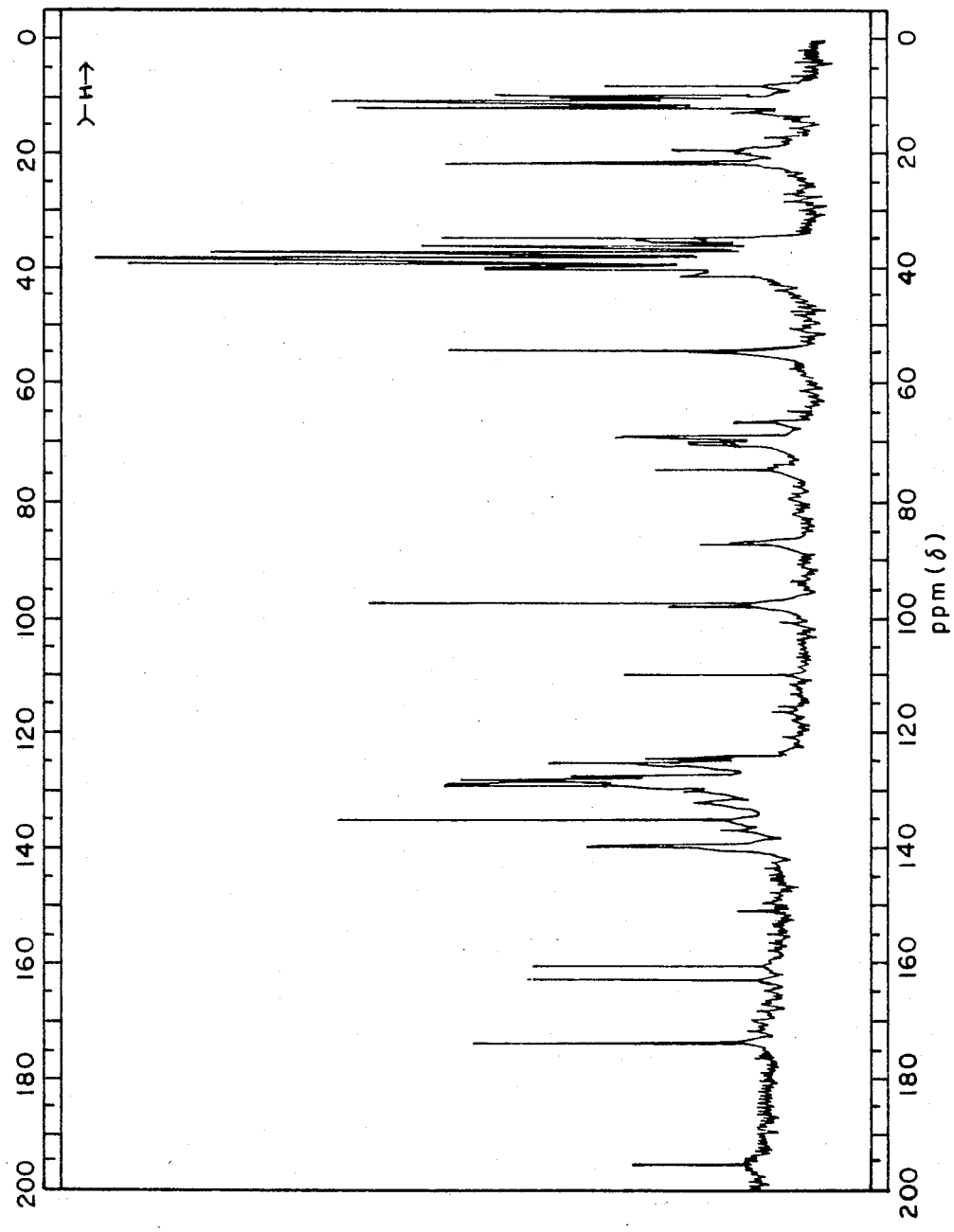
FIGURE III

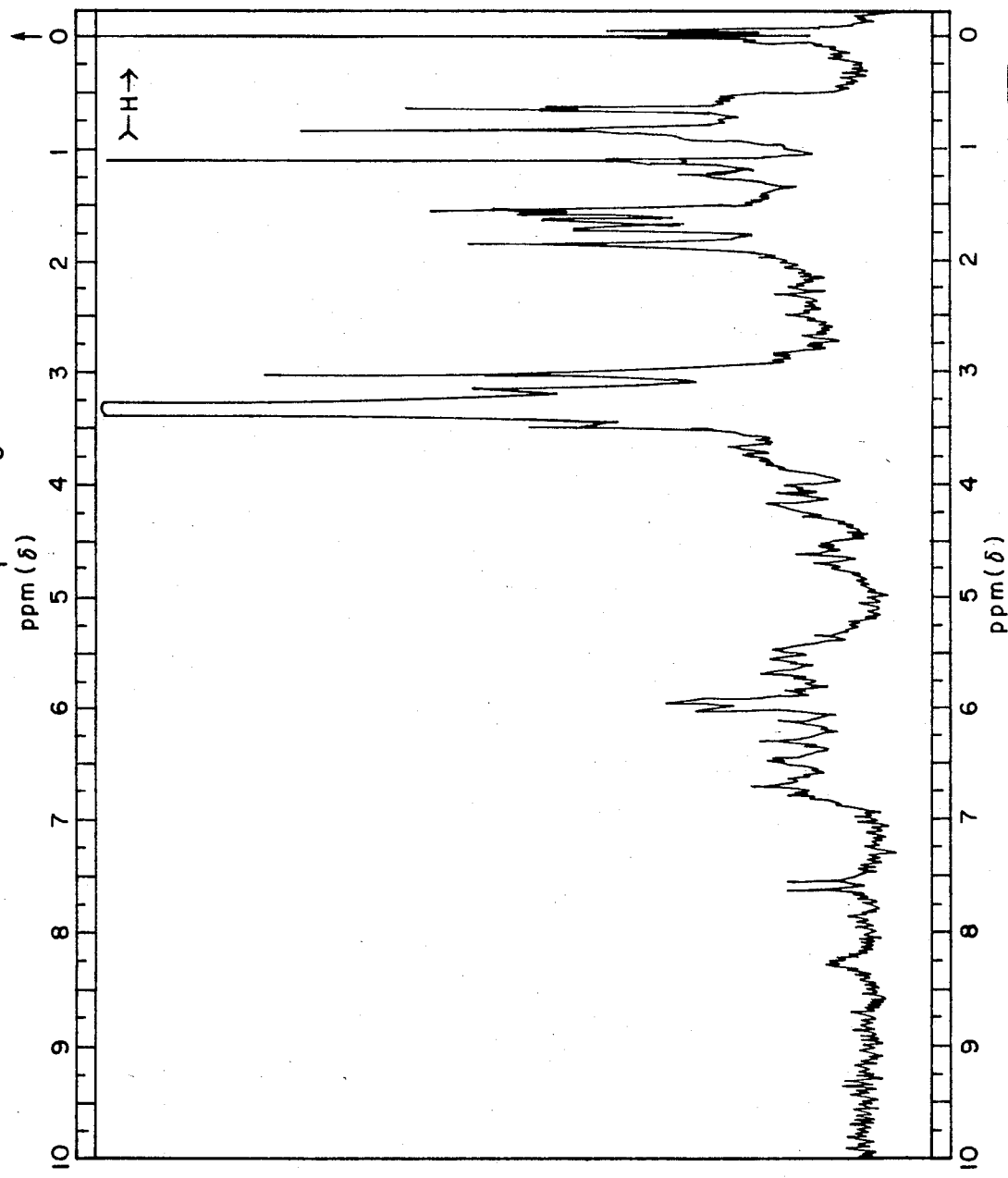

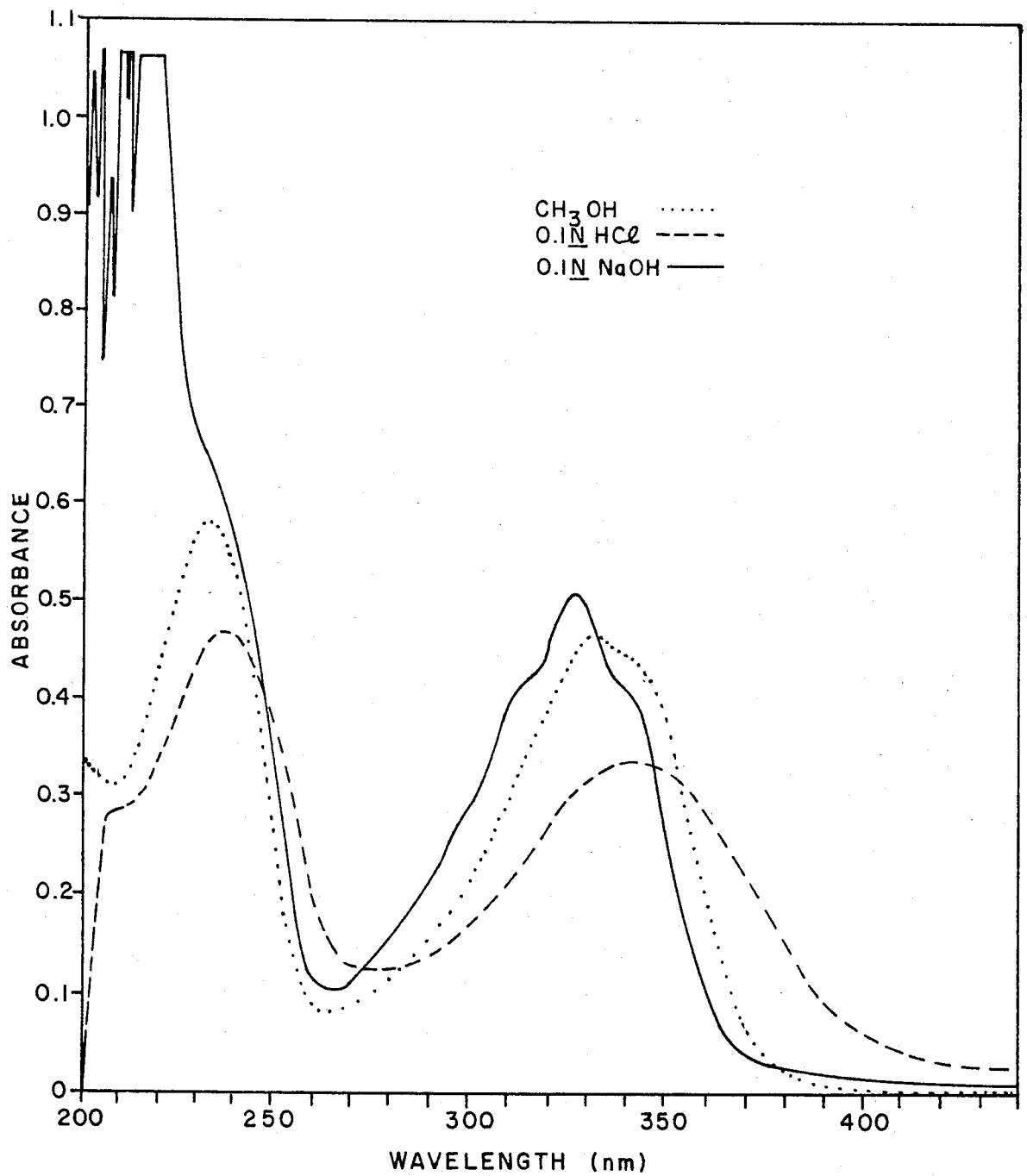
FIGURE V

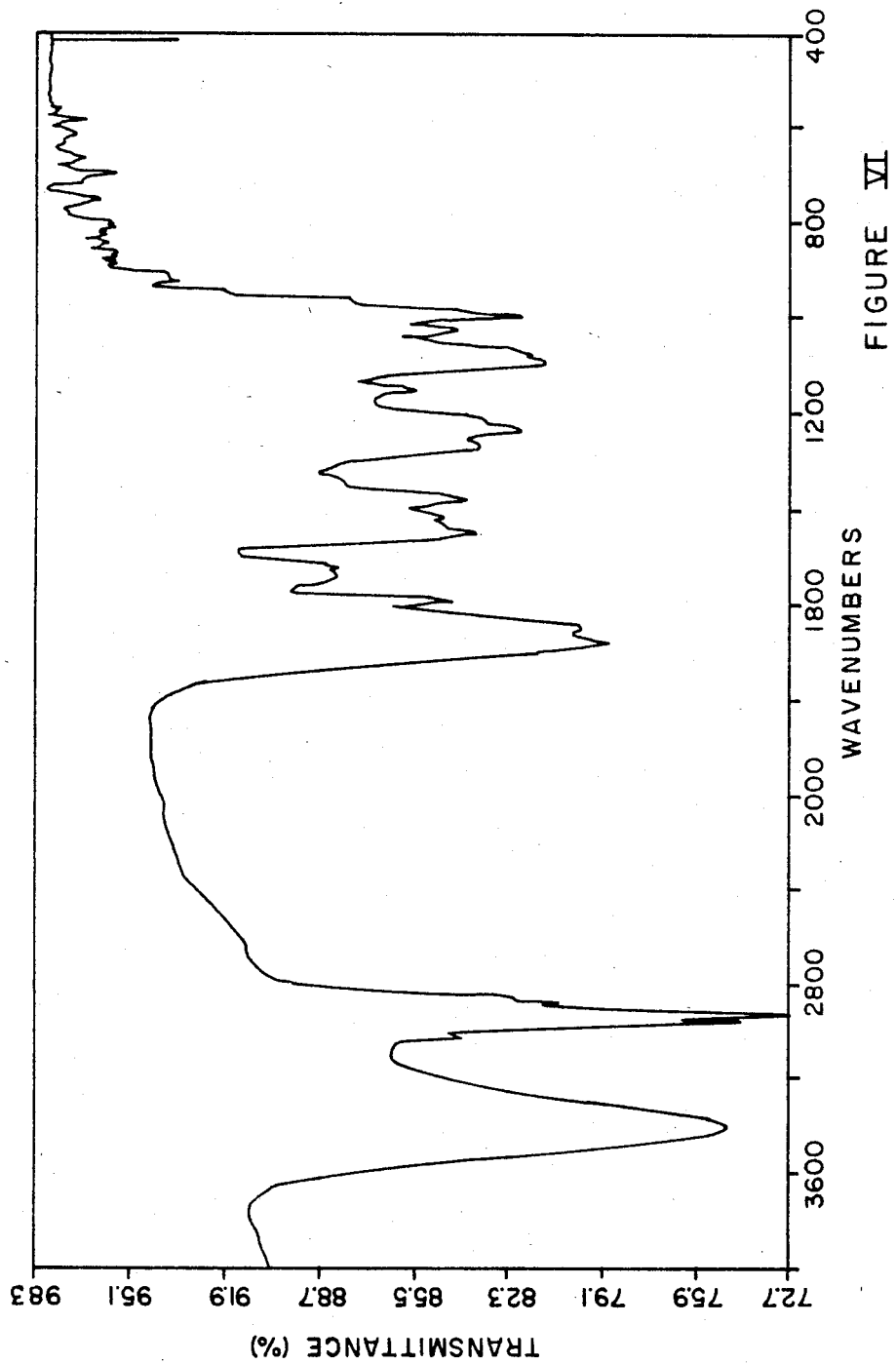

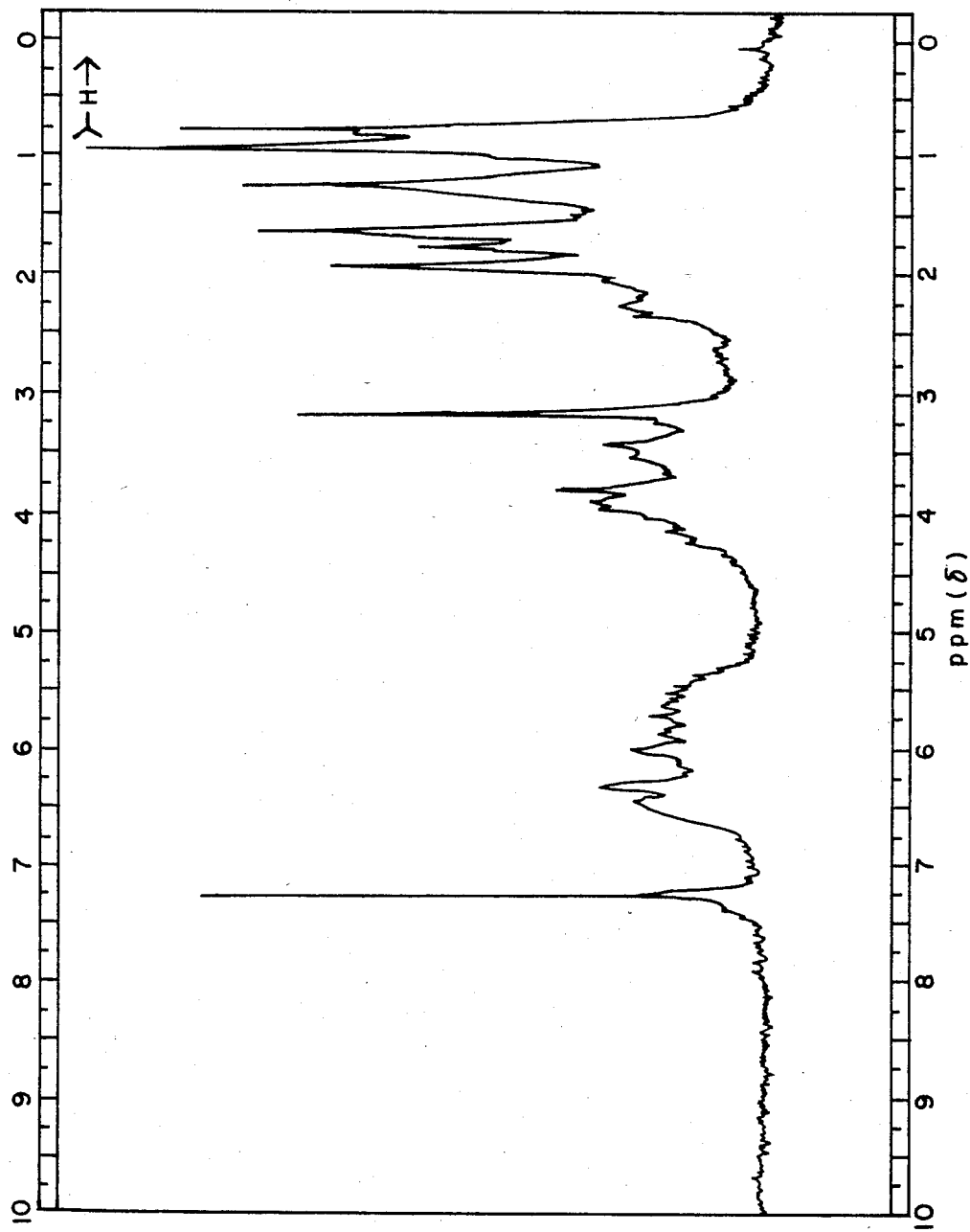

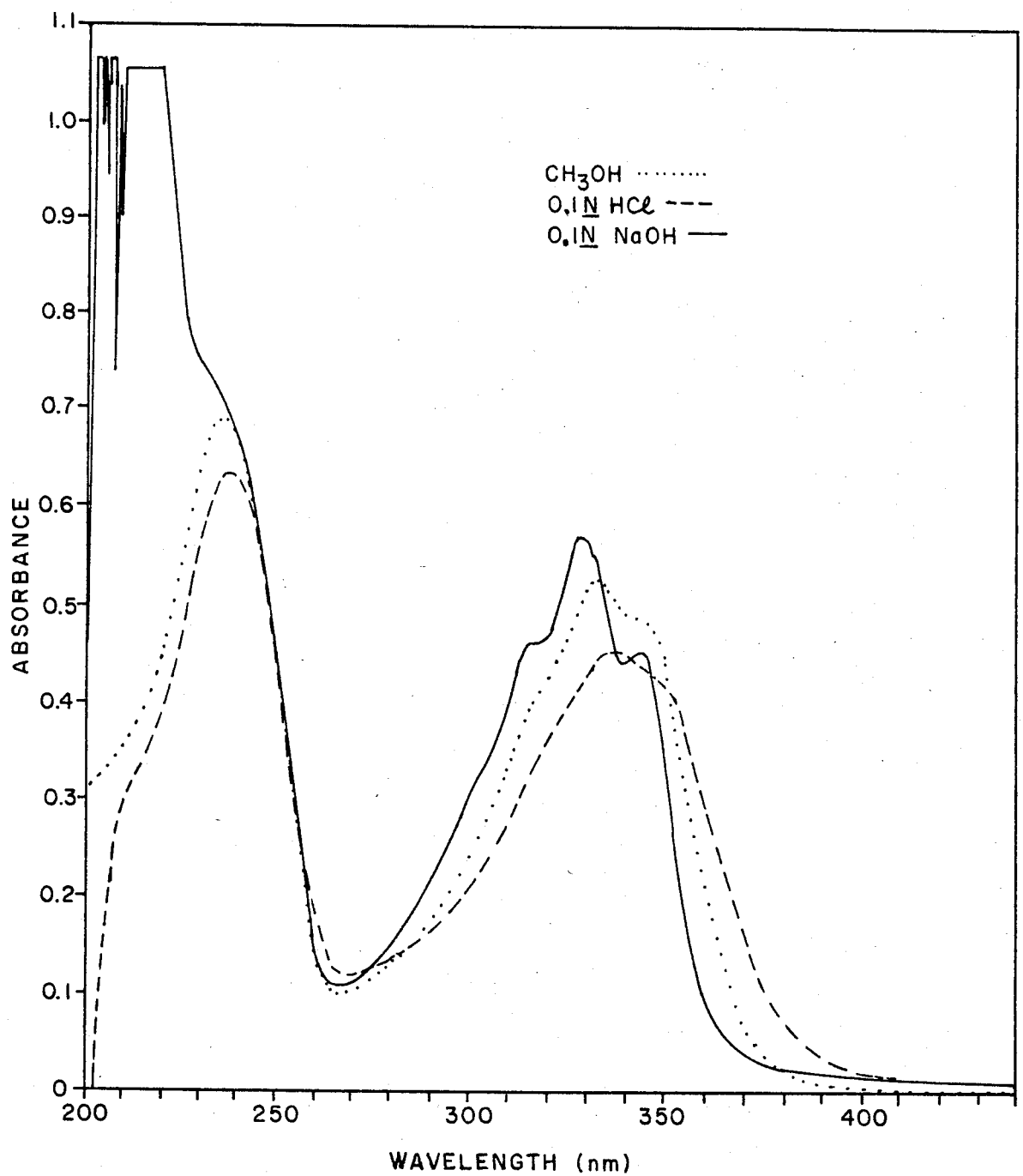
FIGURE VIII

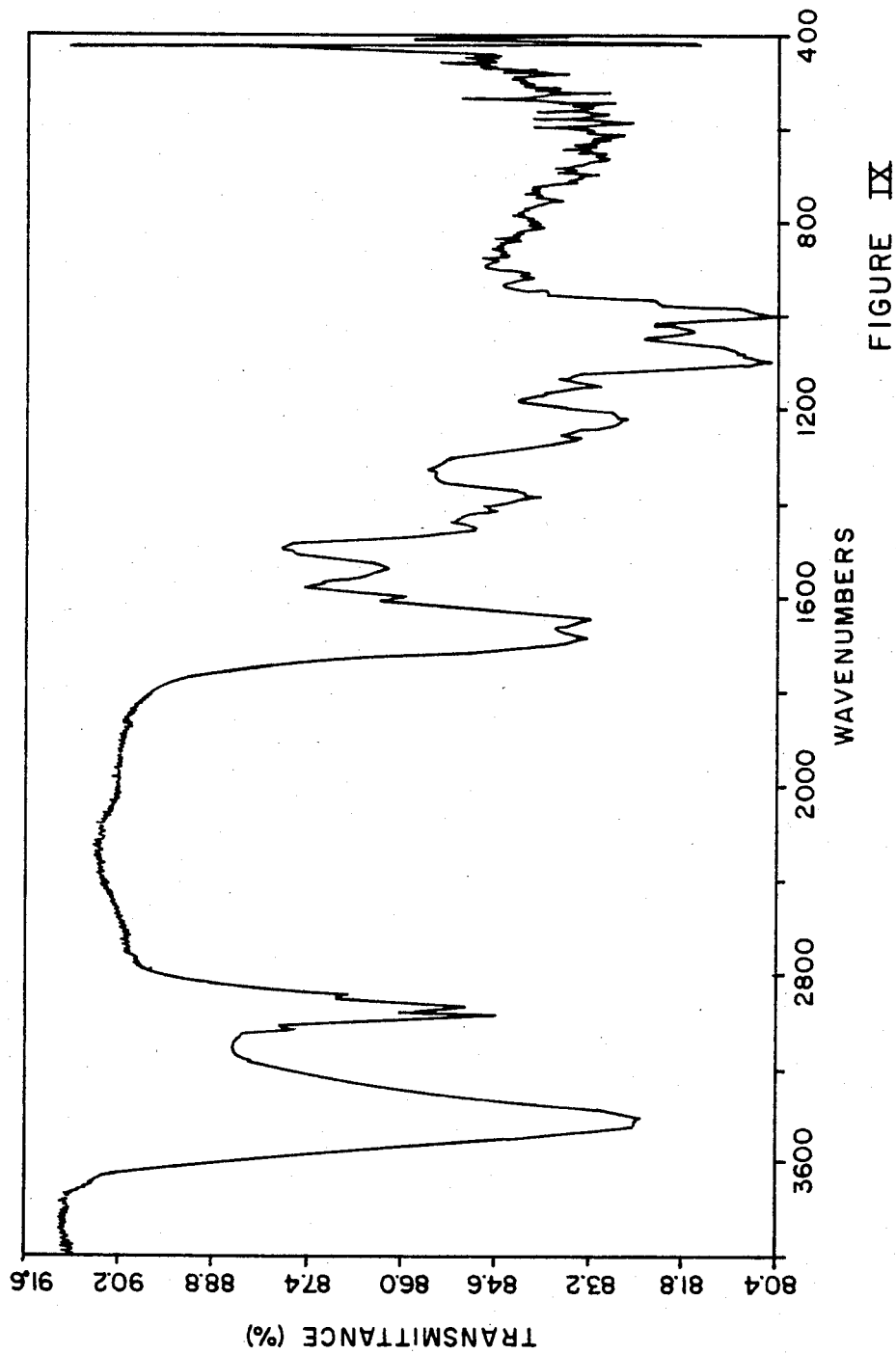

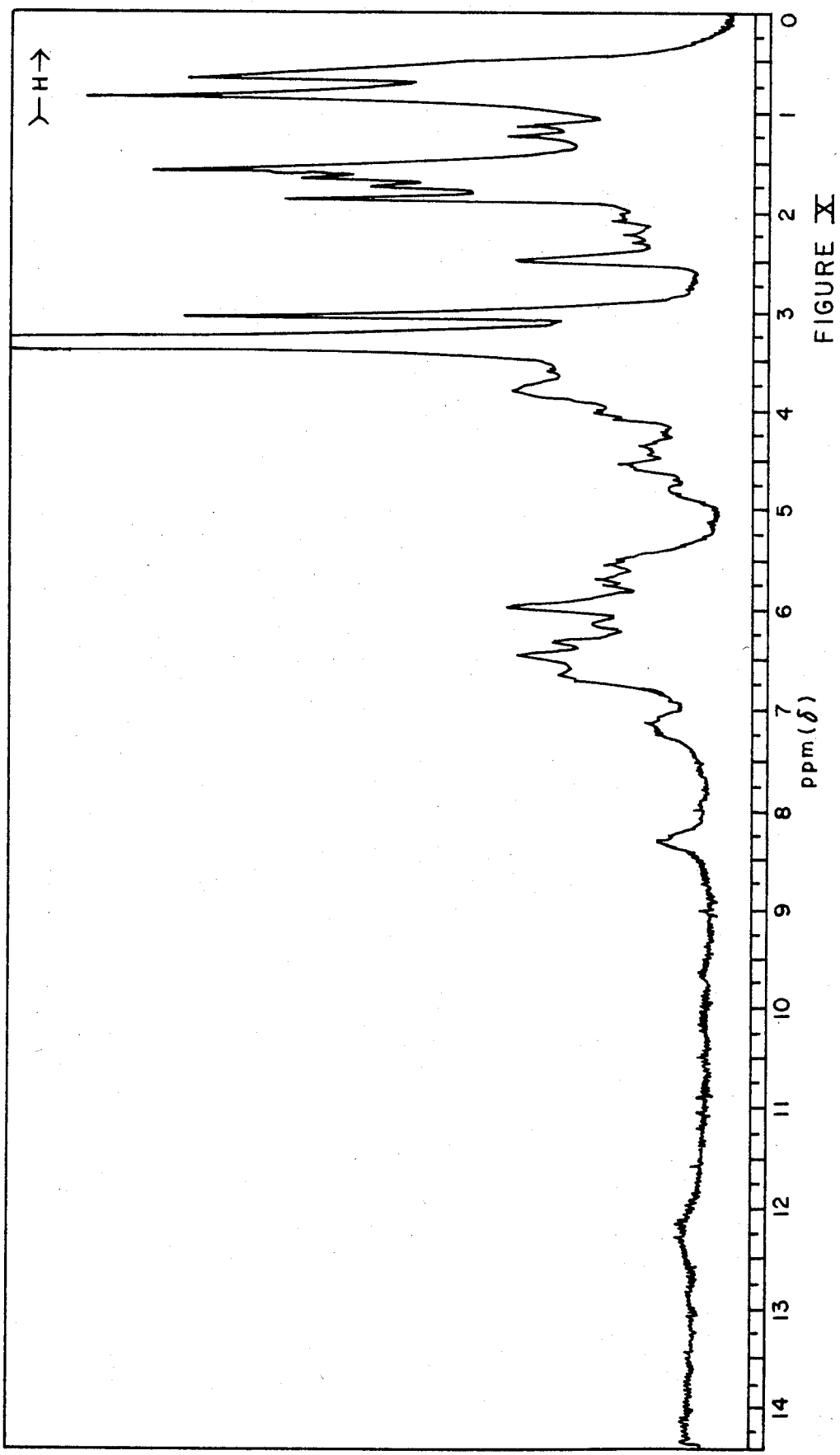

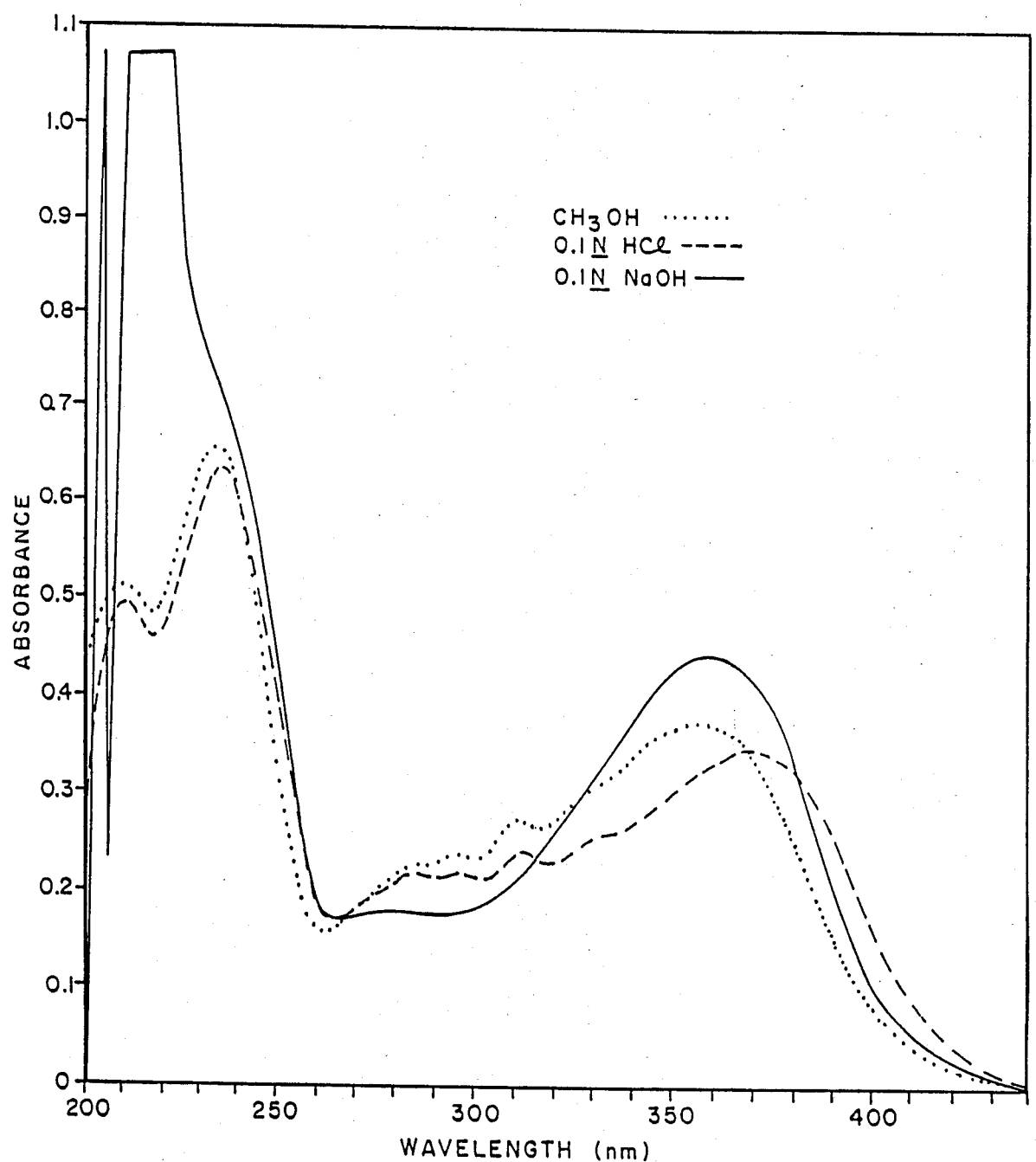
FIGURE XI

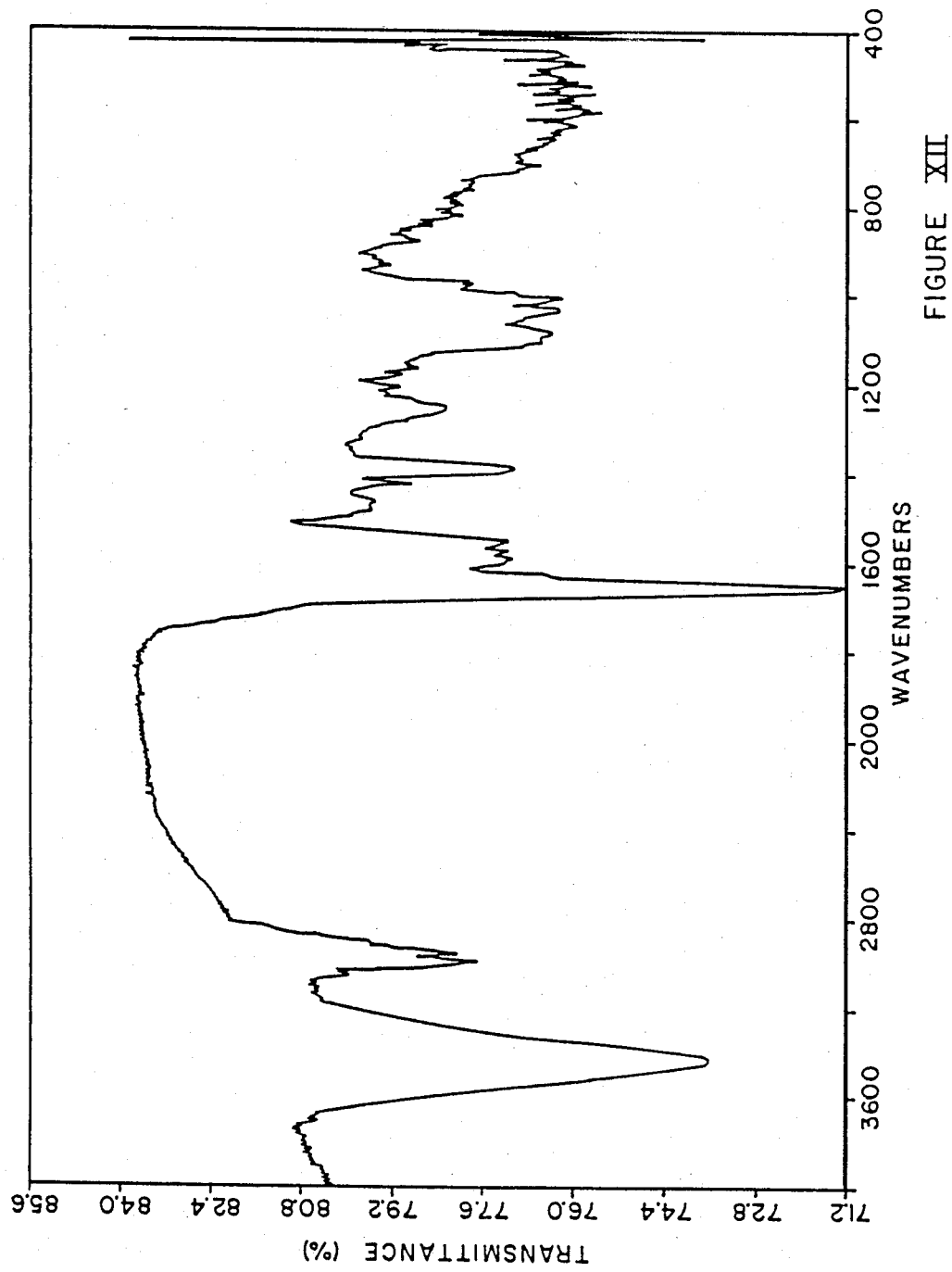

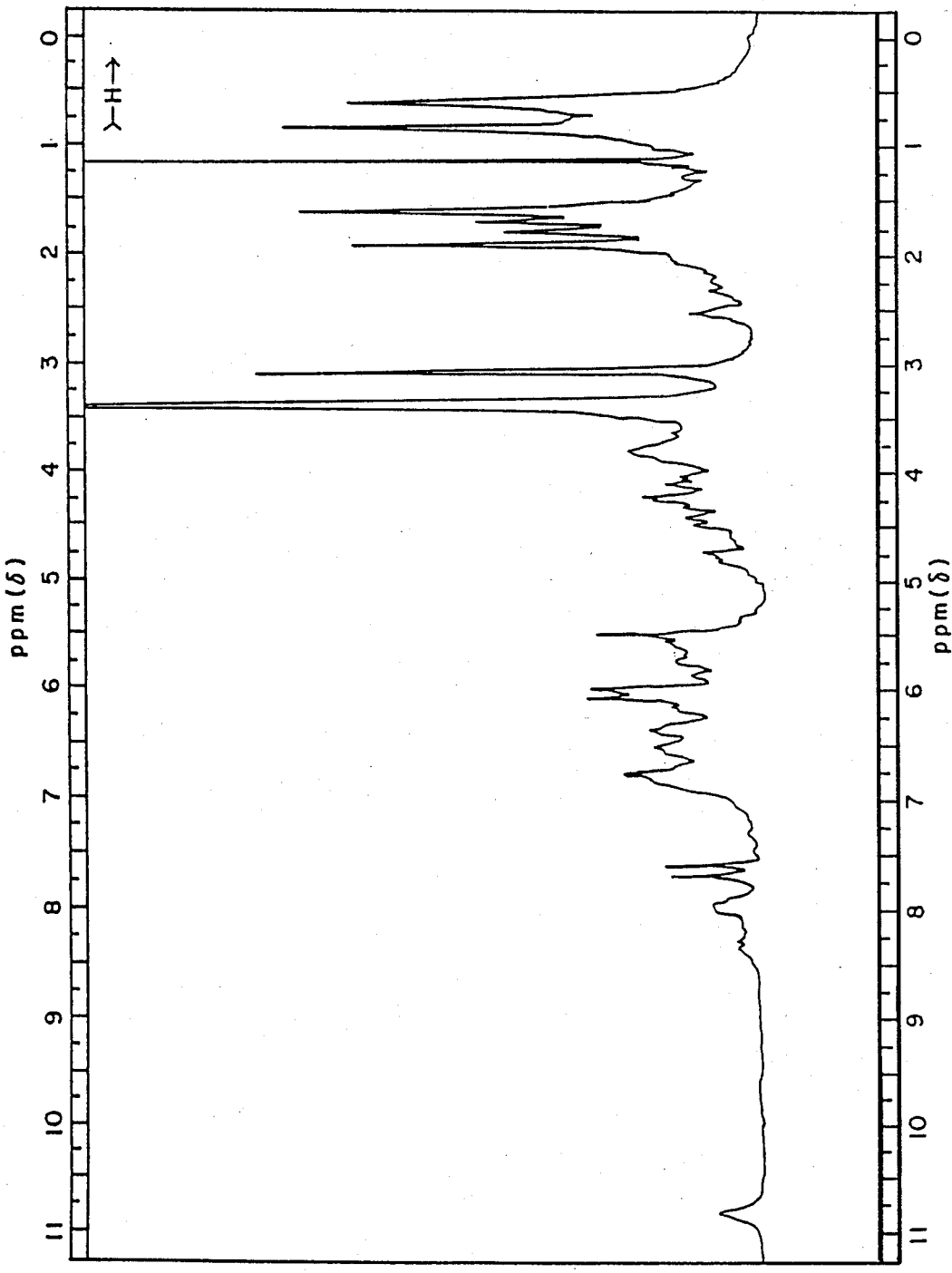

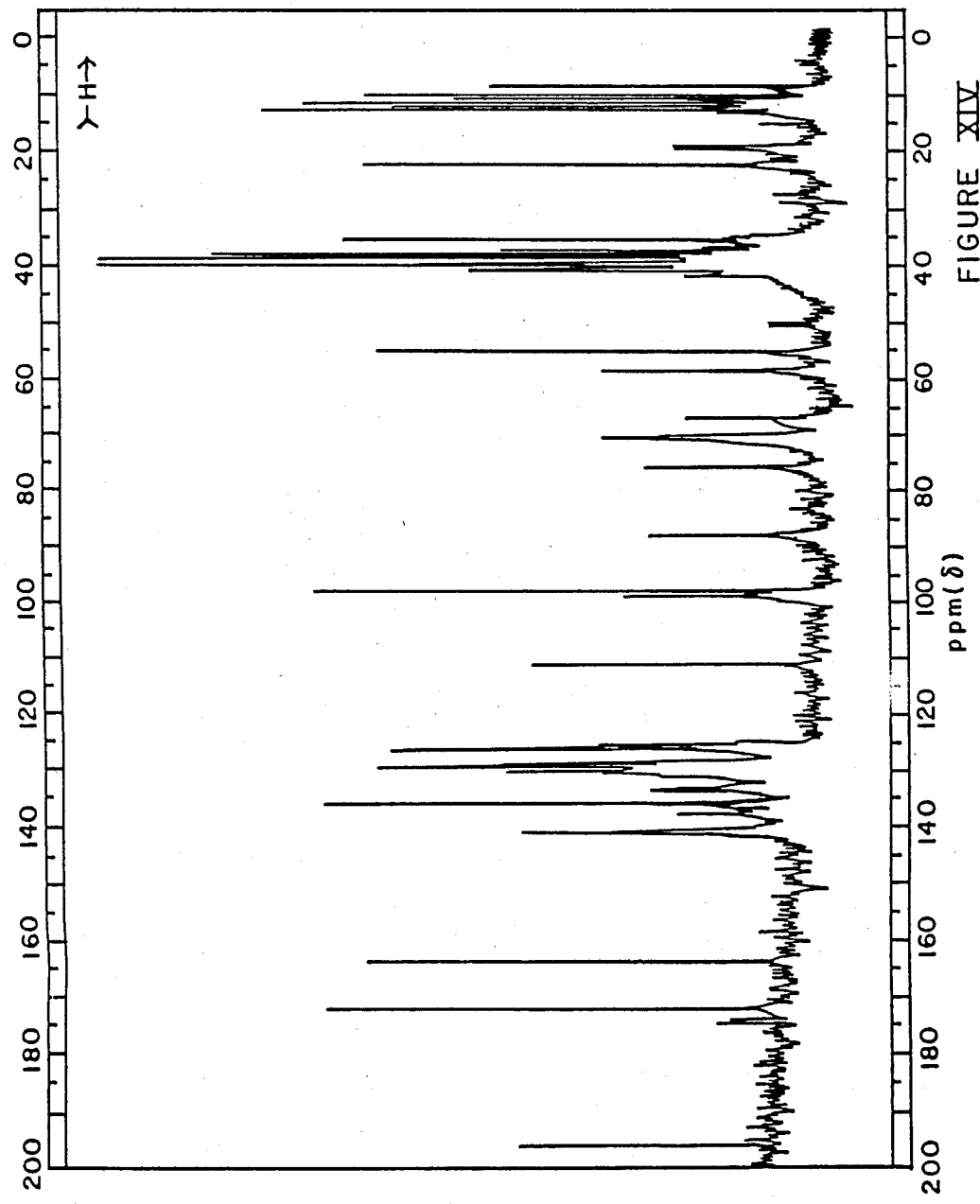

BIOLOGICALLY PORE CULTURE OF *STREPTOMYCES MAJORCIENSIS* LABEDA

This is a division of application Ser. No. 507,184 filed June 23, 1983.

BRIEF SUMMARY OF THE INVENTION

This invention relates to four new antibacterial agents designated LL-C08078$\alpha_1$, LL-C08078$\alpha_2$, LL-C08078$\alpha_3$ and LL-C08078$\beta$; to their production by fermentation, to methods for their recovery and concentration from crude solutions and to processes for their purification. The present invention includes within its scope the antibacterial agents in dilute forms, as crude concentrates and in pure crystalline forms. The effects of the new antibacterial agents on specific microorganisms, together with their chemical and physical properties, differentiate them from previously described antibacterial agents.

The molecular structure of these antibacterial agents is unknown at the present time.

DETAILED DESCRIPTION OF THE INVENTION

The new antibacterial agents designated LL-C08078$\alpha_1$, LL-C08078$\alpha_2$, LL-C08078$\alpha_3$ and LL-C08078$\beta$ are formed during the cultivation under controlled conditions of a new strain of a new species of Streptomyces named *Streptomyces majorciensis* Labeda, sp. nov. This new antibiotic producing strain is maintained in the culture collection of the Lederle Laboratories Division, American Cyanamid Company, Pearl River, N.Y. as culture number LL-C08078. A viable culture of the new microorganism has been deposited with the Patent Culture Collection, Fermentation Laboratory, Northern Regional Research Center, United States Department of Agriculture, Peoria, Ill., and has been added to its permanent collection. It is freely available to the public from this depository under its accession number NRRL 15167.

The new antibiotics LL-C08078$\alpha_1$ and LL-C08078$\beta$ have now been discovered to be members of the Aurodox family of antibiotics [Can. J. Chem., 58: 501–526 (1980)] but are the only members other than antibiotic A40A (U.S. Pat. No. 4,264,407) that contain a tetraene as a part of the chromophore. LL-C08078$\alpha_1$ and A40A have optical rotations of opposite sign and differ significantly in their $^{13}$C NMR spectra in the 95–115 ppm region when the spectra are run in methanol. LL-C08078$\beta$ shows a significant difference from A40A in optical rotation and has a $^{13}$C NMR spectrum very similar to LL-C08078$\alpha_1$.

The following is a comparison of Aurodox, LL-C08078$\alpha_1$ and LL-C08078$\beta$ $^{13}$C NMR chemical shifts. The $^{13}$C NMR spectra (20 MHz) of the antibiotics in the free acid form were run in DMSO-$d_6$ with tetramethylsilane (TMS) as an internal reference. Peak positions are given below in parts per million from TMS. Not all overlapping peaks are indicated for LL-C08078$\alpha_1$ and LL-C08078$\beta$.

| Aurodox | LL-C08078$\alpha_1$ | LL-C08078$\beta$ |
|---|---|---|
| 195.6 | 195.2 | 195.2 |
| 175.4 | 174.0 | 171.6 |
| 163.0 | 163.2 | 163.2 |
| 160.0 | 160.8 | 160.8 |
| 139.9 | 140.4 | 140.5 |
| 139.9 | 140.1 | 140.5 |
| 139.7 | 140.1 | 140.1 |
| 136.3 | 137.6 | 137.6 |
| 135.6 | 135.7 | 135.7 |
| 134.6 | 133.1 | 135.3 |
| 130.9 | 132.7 | — |
| 129.9 | 129.8 | 130.8 |
| 129.9 | 129.8 | 130.1 |
| 129.0 | 129.0 | 129.1 |
| 128.3 | 128.1 | 128.2 |
| 127.5 | 127.8 | — |
| 126.0 | 126.0 | 126.0 |
| 125.2 | 125.9 | 126.0 |
| 124.6 | 125.1 | 124.9 |
| 109.4 | 110.7 | 110.7 |
| 99.4 | 97.9 | 97.4 |
| 98.3 | 98.7 | 98.6 |
| 89.0 | 87.7 | 87.8 |
| 80.1 | — | — |
| 79.2 | — | — |
| 74.9 | 75.4 | 75.7 |
| 72.7 | — | — |
| 72.1 | — | — |
| 71.3 | 71.0 | 71.0 |
| 69.3 | 69.9 | 70.3 |
| — | 67.3 | 67.4 |
| 55.2 | 55.2 | 58.5 |
| 49.2 | 55.4 | 55.5 |
| 40.0 | 40.0 | 40.0 |
| 38.1 | 38.6 | 38.8 |
| 35.6 | 35.9 | 35.8 |
| 34.5 | 35.2 | 35.2 |
| 23.8 | 22.4 | 22.4 |
| 19.3 | 20.2 | 19.5 |
| 15.3 | — | — |
| 12.8 | 13.0 | 13.1 |
| 12.1 | 11.9 | 12.2 |
| 11.4 | 11.8 | 11.8 |
| 10.9 | 11.1 | 11.1 |
| 10.6 | 10.5 | 10.5 |
| — | 8.8 | 8.8 |

Culture LL-C08078, which produced a novel antibiotic with rumen growth promotant activity, was isolated from a soil sample collected in Majorca, Spain. The culture was taxonomically characterized and was identified as a new species of the red-series Streptomyces to be known as *Streptomyces majorciensis* Labeda, sp. nov. Observations were made of the cultural, physiological and morphological features of the culture in accordance with methods detailed by E. B. Shirling and D. Gottlieb, Methods for characterization of Streptomyces species. Internat. J. Syst. Bacteriol. 16: 313–340 (1967). Media used in this study were selected from those recommended by T. G. Pridham, et al., A selection of media for maintenance and taxonomic study of Streptomycetes. Antibiotics Ann. pp. 947–953 (1956–57), for the taxonomic study of actinomycetes. Chemical composition of the cell walls of the culture was determined by using the method of H. A. Lechevalier, et al., Chemical composition as a criterion in the classification of Actinomycetes. Adv. Appl. Microbiol. 14: 47–72 (1971). Details are recorded in Tables I–IV, and a general description of the culture is given below. Underscored descriptive colors are taken from K. L. Kelly and D. B. Judd, Color. Universal Language and Dictionary of Names. Nat. Bur. Stand. (U.S.) Spec. Publ. 440, Washington, D.C. (1976) and the accompanying Inter-Society Color Council, Nat. Bur. Stand. Centroid Color Charts.

MICROMORPHOLOGY

Spores are formed in long straight chains (*Rectus flexibilis*) on aerial sporophores. The spores are phlangiform (0.8–0.9 micron by 1.3–1.4 micron) and the surface of the mature spores is smooth when observed by scanning electron microscopy.

CELL WALL COMPOSITION

Whole cell hydrolysates of this culture contain the L,L-isomer of diaminopimelic acid, placing it in the Type I cell wall group of Lechevalier, et al., (vide supra). This is typical of all Streptomyces species.

AMOUNT OF GROWTH

Good growth is observed on all media.

AERIAL MYCELIUM AND SPORE COLOR

Aerial mycelium is white; spore masses are pinkish gray shades, ranging from 10. pinkish gray to 8. grayish pink. Sporulation is heavy to very heavy, depending on the medium.

SOLUBLE PIGMENTS

Absent on many media; brownish shades where produced.

REVERSE COLOR

Yellow to yellowish brown shades on all media.

PHYSIOLOGICAL REACTIONS

Nitrates not reduced to nitrites; weak liquification of gelatin in 14 days; black pigment produced on peptone-yeast extract-iron agar but not on tyrosine medium in 7 days. Carbohydrate utilization as per the method of T. G. Pridham and D. Gottlieb, the utilization of carbon compounds by some Actinomycetales as an aid for species determination, J. Bacteriol. 56:107–114 (1948): good utilization of galactose, glucose, glycerol, maltose, mannose and trehalose; poor utilization of fructose and salicin; no utilization of adonitol, arabinose, dulcitol, inositol, lactose, mannitol, melezitose, melibiose, raffinose, rhamnose, sorbitol, sucrose, xylose.

Culture LL-C08078 was compared with Streptomyces reference cultures from the aforesaid Lederle culture collection which are known to produce antibiotics of this class and a reference culture of the red-spored streptomycete group closest to this strain. The following observations were made of 14-day growth on yeast extract-malt extract agar:

| Culture | Spore Mass Color | Soluble Pigments | Reverse Color |
|---|---|---|---|
| RC47 *S. goldiensis* ATCC 21386 | light gray | none | pale yellow |
| RC52 *S. filipinensis* NRRL11044 | light gray | none | pale yellow |
| RC97 *S. xanthophaeus* NRRLB5414 | no sporulation | none | yellowish white |
| LL-C08078 *S. majorciensis* | pinkish gray | none | yellow brown |

Culture LL-C08078 resembles none of the Streptomyces species producing antibiotics of the mocimycin class. Moreover, it resembles no described species of the genus Streptomyces, and thus, based on the observations presented, a new species is proposed to be called *Streptomyces majorciensis* Labeda, sp. nov.

TABLE I

Cultural Characteristics of LL-C08078
Incubation: 14 Days
Temperature: 28° C.

| Medium | Amount of Growth | Aerial Mycelium and/or Spores | Soluble Pigment | Reverse color |
|---|---|---|---|---|
| Glycerol-Asparagine Agar | Good to Moderate | Plicate growth with heavy sporulation; spore mass 10. pinkish gray. | None | Pale yellow |
| Hickey-Tresner Agar | Good | Raised, mounded colonies; Sporulation heavy; spore masses 10. pinkish gray with tufts of white aerial mycelia | Brownish | Dark yellowish brown |
| Inorganic Salts-Starch Agar | Good | Heavy sporulation; spore mass 10. pinkish gray | Brownish | Pale yellow |
| Oatmeal Agar | Good | Heavy sporulation; 10 pinkish gray to 8. grayish pink; white tufts of aerial mycelia. | None | Pale yellow |
| Tomato Paste Oatmeal Agar | Good | Very heavy sporulation on raised colonies; spore mass 10. pinkish gray; scattered tufts of white aerial mycelia. | Brownish | — |
| Yeast Extract Malt Extract Agar | Good | Heavy sporulation; 10. pinkish gray. | None | Strong yellowish brown |

TABLE II

Micromorphology of LL-C08078

| Medium | Aerial Mycelium and/or Sporiferous Structures | Spore Shape | Spore Size | Spore Surface |
|---|---|---|---|---|
| Yeast Extract Malt Extract Agar | Spore chains arise as straight chains from aerial sporophores (*Rectus flexibilis*) | phlangiform | 0.8–0.9 micron × 1.3–1.4 microns | Smooth |

TABLE III

Physiological Reactions of LL-C08078

| Medium | Incubation Period (Days) | Amount of Growth | Physiological Reaction |
|---|---|---|---|
| Peptone - Iron Agar | 7 | Good | Blackening |
| | 14 | Good | Blackening |
| Tyrosine Agar | 7 | Good | No pigment |
| | 14 | Good | No pigment |
| Litmus Milk | 7 | Good | Moderate proteolysis |
| | 14 | Good | Strong proteolysis |

TABLE III-continued

Physiological Reactions of LL-C08078

| Medium | Incubation Period (Days) | Amount of Growth | Physiological Reaction |
|---|---|---|---|
| Nutrient Gelatin | 7 | Good | No proteolysis |
| | 14 | Good | Weak proteolysis |
| Nitrate Broth | 14 | Good | No reduction |
| Esculin Broth | 7 | Good | Hydrolysis |
| Urea Broth | 14 | Good | No hydrolysis |

TABLE IV

Carbon Source Utilization of LL-C08078

Incubation: 14 Days  Temperature: 28° C.

| Carbon Source: | Utilization* |
|---|---|
| Adonitol | 0 |
| l-Arabinose | 0 |
| Dulcitol | 0 |
| Fructose | 1 |
| d-Galactose | 3 |
| d-Glucose | 3 |
| Glycerol | 3 |
| i-Inositol | 0 |
| Lactose | 0 |
| Maltose | 3 |
| Mannose | 3 |
| d-Mannitol | 0 |
| Melezitose | 0 |
| Melibiose | 0 |
| d-Raffinose | 0 |
| l-Rhamnose | 0 |
| Salicin | 1 |
| Sorbitol | 0 |
| Sucrose | 0 |
| Trehalose | 3 |
| Xylose | 0 |
| Negative control | 0 |

*3 = Good utilization
2 = Fair utilization
1 = Poor utilization
0 = No utilization It is to be understood that for the production of these new antibacterial agents, the present invention is not limited to this particular organism or to organisms fully answering the above growth and microscopic characteristics, which are given for illustrative purposes only. In fact, it is desired and intended to include in the term "Streptomyces majorciensis Labeda, sp. nov., NRRL 15167" the natural (spontaneous) mutants of this organism as well as induced mutants produced from this organism by various mutagenic means known to those skilled in the art, such as exposure to X-ray radiation, ultraviolet irradiation, nitrogen mustard, actinophages, nitrosamines and the like. It is also desired and intended to include inter- and intra-specific genetic recombinants produced by genetic techniques known to those skilled in the art, such as, for example, conjugation, transduction, and genetic engineering techniques.

The antibacterial agents were tested in vitro using a variety of gram-positive bacteria by the standard agar dilution procedure. The results are reported as minimal inhibitory concentrations (mcg/ml) in Table V.

TABLE V

In Vitro Anitbacterial Activity

| | Minimal Inhibitory Conc. (mcg/ml) | | |
|---|---|---|---|
| Organism | LL-C08078$\alpha_1$ | LL-C08078$\alpha_3$ | LL-C08078$\beta$ |
| Streptococcus β-hemolytic C203 | 8 | 8 | 32 |
| Streptococcus β-hemolytic 636TCR | 16 | 256 | 64 |
| Streptococcus β-hemolytic AGB | 16 | 256 | 128 |
| Sarcina lutea PCI1001 | 128 | | 128 |
| Corynebacterium minutissimum LL No. 151 | 256 | 128 | 128 |

These compounds are also active in vivo as evidenced by their effectiveness against lethal infections in warm-blooded animals. LL-C08078$\alpha_1$ is active when administered subcutaneously to mice which have been infected with a lethal dose of Streptococcus pyogenes C203. The ED$_{50}$ for LL-C08078$\alpha_1$ is 131 mg/kg of body weight.

These compounds are also active in vivo as growth promoting agents in warm-blooded animals.

Fermentation Process

Cultivation of Streptomyces majorciensis Labeda, sp. nov. NRRL 15167 may be carried out in a wide variety of liquid culture media. Media which are useful for the production of these novel antibacterial agents include an assimilable source of carbon such as starch, sugar, molasses, glycerol, etc.; an assimilable source of nitrogen such as protein, protein hydrolysate, polypeptides, amino acids, corn steep liquor, etc.; and inorganic anion and cation salts, such as potassium, sodium, ammonium, calcium, sulfate, carbonate, phosphate, chloride, etc. Trace elements such as boron, molybdenum, copper, etc., are supplied as impurities of other constituents of the media. Aeration in tanks, bottles and flasks is supplied by forcing sterile air through or onto the surface of the fermenting medium. Further agitation in tanks is provided by a mechanical impeller. An antifoaming agent such as lard oil or silicone defoamer may be added as needed.

Inoculum Preparation

Shaker flask inoculum of Streptomyces majorciensis Labeda, sp. nov. NRRL 15167 is prepared by inoculating 100 ml or 200 ml portions of sterile liquid medium in appropriate flasks with scrapings or washings of spores from an agar slant of the culture. The following is an example of a suitable medium:

| | |
|---|---|
| Corn starch | 1.2% |
| Dextrose | 0.6% |
| Beef extract | 0.3% |
| Yeast extract | 0.5% |
| Bacto ®-tryptone[1] | 0.5% |
| Calcium carbonate | 0.2% |
| Water qs | 100% |

[1]A peptone, registered trademark of Difco Laboratories, Detroit, Michigan]

The pH is adjusted to 7.5 with an alkali metal hydroxide and the mixture is sterilized prior to inoculation.

These flasks are incubated at 25°–29° C., preferably 28° C. and agitated at 180 r.p.m. on a rotary shaker for 30–50 hours. This inoculum is then used to inoculate one liter or 12 liter batches of the same sterile inoculum at the rate of 100 ml per liter or 200 ml per 12 liters, in glass bottles. This bottle inoculum is aerated by a sterile air flow of 10-40 liters per minute while growth is continued at 25°-29° C., preferably 28° C., for 24-50 hours.

These bottle inocula are then used to inoculate 260 liters of the same sterile media in 300 liter tanks. The tank inoculum is grown at 25°-29° C., preferably 28° C., with sterile air flow of 100-200 liters per minute and agitation at 200-300 r.p.m. for 24-50 hours and then used to inoculate tank fermentors.

Tank Fermentation

For the production of these antibacterial agents in tank fermentors the following sterilized medium may be used:

| | |
|---|---|
| Dextrin | 5.0% |
| Dextrose | 0.5% |
| Soy flour | 3.5% |
| Calcium carbonate | 0.7% |
| Cobalt chloride hexahydrate | 0.00025% |
| Water qs | 100% |

Each tank is inoculated with 3-10% of the tank inoculum described above. Aeration is supplied at the rate of 0.2-0.8 liter of sterile air per liter of media per minute and the fermenting mash is agitated by an impeller driven at 100-200 r.p.m. The temperature is maintained at 25°-29° C., usually 28° C. and the fermentation is normally continued for 75-100 hours, at which time the mash is harvested.

This invention will be described in greater detail in conjunction with the following non-limiting examples.

EXAMPLE 1

Inoculum Preparation

A typical medium used to grow the primary inoculum was prepared according to the following formula:

| | |
|---|---|
| Corn starch | 1.2% |
| Dextrose | 0.6% |
| Beef extract | 0.3% |
| Yeast Extract | 0.5% |
| Bacto ®-tryptone | 0.5% |
| Calcium carbonate | 0.2% |
| Water qs | 100% |

The pH was adjusted to 7.5 with 6N sodium hydroxide and the medium was sterilized at 121° C. for 15 minutes. A 100 ml portion of this sterile medium, in a flask, was inoculated with scrapings from an agar slant of the culture *Streptomyces majorciensis* Labeda, sp. nov. NRRL 15167. The medium was placed on a rotary shaker and agitated vigorously at 180 r.p.m. for 48 hours at 28° C.

The resulting primary inoculum was used to inoculate one liter of the same sterile medium in a 2-liter bottle, which was aerated with sterile air flow of 10 liters per minute and grown at 28° C. for 48 hours, providing secondary inoculum.

Two one-liter portions of this secondary inoculum were used to inoculate 260 liters of the same sterile medium in a 300-liter tank. This tank inoculum was grown at 28° C. with sterile air flow of 150 liters per minute and agitation by an impeller driven at 230 r.p.m. for 24 hours, providing tertiary (tank) inoculum.

EXAMPLE 2

Fermentation

A fermentation medium was prepared according to the following formula:

| | |
|---|---|
| Dextrin | 5.0% |
| Dextrose | 0.5% |
| Soy flour | 3.5% |
| Calcium carbonate | 0.7% |
| Cobalt chloride hexahydrate | 0.00025% |
| Water qs | 100% |

A 2800 liter portion of this medium was sterilized at 121° C. for 60 minutes and then inoculated with 260 liters of the tertiary inoculum described in Example 1. After sterilization, pH is 7.0. Aeration was supplied at the rate of 1650 liters of sterile air per minute and agitation was supplied by an impeller driven at 100 r.p.m. The temperature was maintained at 28° C. and the fermentation was terminated after 88 hours at which time the mash was harvested.

EXAMPLE 3

Preliminary Isolation of LL-C08078$\alpha_1$, $\alpha_2$, $\alpha_3$ and $\beta$ A harvest mash, prepared as described in Example 2, comprising 2950 liters was extracted with 1125 liters of methylene chloride. The organic extract was then concentrated in vacuo to a residue, giving 767 g (Solid A). The remaining aqueous portion was reextracted with 1000 liters of fresh methylene chloride and this organic extract was concentrated in vacuo to a residue, giving 646 g (Solid B).

The solid (A) was suspended in a mixture of 2 parts ether and one part hexane and shaken gently. The mixture was allowed to separate and the liquid portion was removed by decantation. The residue was dissolved in methylene chloride and then concentrated in vacuo to a residue, giving 241 g (Solid C).

A harvest mash, prepared as described in Example 2, comprising 3000 liters, was extracted with 1200 liters of methylene chloride. The organic extract was concentrated in vacuo to a residue, giving 426 g (Solid D).

The solids B, C and D were combined (total weight 1313 g) and suspended in ether. This suspension was filtered and the solid was washed with ether and dried, giving 309 g of combined components LL-C08078$\alpha_1$, $\alpha_2$, $\alpha_3$ and $\beta$.

EXAMPLE 4

Isolation of LL-C08078$\alpha_1$

A glass column with a diameter of 3 inches was filled to a height of 20 inches with silica gel. A 12 g portion of the product of Example 3 was stirred with 100 ml of ethyl acetate, filtered and the filtrate allowed to seep into the column. The column was developed with 1.2 liters of ethyl acetate and then with ethyl acetate containing 5% of absolute ethanol. Fractions of 75 ml each were collected and monitored for activity by bioautography against B. cereus. Fractions 72-120 were combined and concentrated in vacuo, giving 2.311 g of a solid.

A glass column with a diameter of 9 inches was packed to a height of 20 inches with silica gel. A 218 g portion of the product of Example 3 was stirred with 2 liters of ethyl acetate, filtered and the filtrate allowed to seep into the column. The charge was washed in with 13 liters of fresh ethyl acetate and the column was then developed with ethyl acetate containing 8% ethanol. Fractions of 4 liters each were collected and checked for activity as described above, then the column was stripped with 50 liters of ethyl acetate:ethanol (8:12). Fractions 1 and 2 were saved for use in Example 5. Fractions 11–19 were combined and concentrated in vacuo to a yellow residue, weighing 24 g.

The above two solids were combined giving 26 g of LL-C08078$\alpha_1$, having the following characteristics:

Elemental analysis: C, 65.95; H, 8.06; N, 3.21; O, 23.16;

$$[\alpha]_D^{26} = -44° \pm 2 \ (0.496\% \text{ in chloroform})$$
$$= -89° \pm 1 \ (0.790\% \text{ in methanol});$$

UV spectra as shown in FIG. I:
10 mcg/ml in methanol
10 mcg/ml in 0.1N HCl
10 mcg/ml in 0.1N NaOH;
An IR spectrum in kBr as shown in FIG. II;
A $^{13}$C NMR Spectrum 20 MHz in d$_6$ DMSO with reference equivalent to internal TMS standard as shown in FIG. III;
A Proton NMR Spectrum 80 MHz in d$_6$ DMSO with internal TMS reference standard as shown in FIG. IV;
Molecular weight by mass spectroscopy 778.

EXAMPLE 5

Isolation of LL-C08078$\alpha_2$ and $\alpha_3$

A glass column with a diameter of 9 inches was packed to a height of 20 inches with silica gel. The fractions 1 and 2 (4 liters each) saved in Example 4 were combined and concentrated in vacuo, giving 42 g of an oily residue. This residue was dissolved in ethyl acetate and charged on a silica gel column. The column was eluted with ethyl acetate, checking the fractions for activity by bioautography. Fractions 1–60 were combined and lyophilized giving 25.0 g of solid. This solid was dissolved in 20 ml of chloroform and allowed to seep into a ¾ inch by 16 inch column of silica gel. The charge was washed in with 100 ml of chloroform and then the column was developed first with chloroform:acetone (4:1) (fractions 1–50) and then with chloroform:acetone (3:2). Fractions of 15 ml each were collected and checked for activity by bioautography.

Fractions 71–75 were combined and concentrated in vacuo to a residue which was lyophilized from t-butanol, giving 64 mg of LL-C08078$\alpha_3$.

Fractions 79–84 were combined and concentrated in vacuo, giving 99 mg of LL-C08078$\alpha_2$.

LL-C08078$\alpha_3$ has the following characteristics:
Elemental analysis: C, 67.99; H, 8.60; N, 1.14;
$[\alpha]_D^{26} = -31° \pm 5$ (0.163% is methanol);
UV Spectra as shown in FIG. V:
10 mcg/ml in methanol
10 mcg/ml in 0.1N HCl
10 mcg/ml in 0.1N NaOH;
An IR spectrum in KBr as shown in FIG. VI;
A Proton NMR Spectrum 80 MHz in CDCl$_3$ with reference equivalent to internal TMS standard as shown in FIG. VII. LL-C08078$\alpha_2$, has the following characteristics:
Elemental analysis: C, 65.02; H, 8.03; N, 1.54;
$[\alpha]_D^{26} = -32° \pm 5$ (0.280% in methanol);
UV Spectra as shown in FIG. VIII:
10 mcg/ml in methanol
10 mcg/ml in 0.1N HCl
10 mcg/ml in 0.1N NaOH;
An IR Spectrum in KBr as shown in FIG. IX;
A Proton NMR Spectrum 80 MHz in d$_6$ DMSO with reference equivalent to internal TMS standard as shown in FIG. X.

EXAMPLE 6

Isolation of LL-C08078$\beta$

A glass column with a diameter of 3 inches was filled to a height of 20 inches with silica gel. A 12 g portion of the product of Example 3 was stirred with 100 ml of ethyl acetate and filtered. The filtrate was allowed to seep into the column which was then developed first with 1.2 liters of ethyl acetate, then with ethyl acetate containing 5% absolute ethanol and collecting a total of 150 fractions of 75 ml each. The column was then stripped with ethyl acetate:methanol (1:1) and this strip was concentrated in vacuo, giving 1.733 g of solid. A 500 mg portion of this solid was dissolved in one ml of chloroform and allowed to seep into a ¾ inch column packed to a height of 40 cm with silica gel. The charge was washed in with 25 ml of chloroform and the column was then developed with chloroform:acetone (1:1) collecting fractions of 20 ml each and monitoring for activity by bioautography. Fractions 13–22 were combined, desolventized and lyophilized, giving 320 mg of LL-C08078$\beta$, having the following characteristics:

Elemental analysis: C, 65.82; H, 7.92; N, 3.62;

$$[\alpha]_D^{26} = -29° \pm 4 \ (0.245\% \text{ in chloroform})$$
$$= -120° \pm 5 \ (0.175\% \text{ in methanol});$$

UV Spectra as shown in FIG. XI:
10 mcg/ml in methanol
10 mcg/ml in 0.1N HCl
10 mcg/ml in 0.1N NaOH;
An IR Spectrum in KBr as shown in FIG. XII;
A Proton NMR Spectrum 80 MHz in d$_6$ DMSO with reference equivalent to internal TMS standard as shown in FIG. XIII;
A $^{13}$C NMR Spectrum 20 MHz in d$_6$ DMSO with reference equivalent to internal TMS standard as shown in FIG. XIV.

We claim:

1. A biologically pure culture of the microorganism *Streptomyces majorciensis* Labeda, sp. nov., having the identifying characteristics of NRRL 15167, said culture being capable of producing the antibiotic LL-C08078$\alpha_1$, LL-C08078$\alpha_2$, LL-C08078$\alpha_3$ or LL-C08078$\beta$ in recoverable quantity upon fermentation in an aqueous nutrient medium containing assimilable sources of carbon, nitrogen and inorganic anion and cation salts.

2. The biologically pure culture of the microorganism *Streptomyces majorciensis* Labeda, sp. nov., according to claim 1, wherein said microorganism has spontaneously mutated such that the microorganism is genetically altered but still retains the ability to synthesize the antibiotic LL-C08078$\alpha_1$, LL-C08078$\alpha_2$, LL-C08078$\alpha_3$ or LL-C08078$\beta$.

3. The biologically pure culture of the microorganism *Streptomyces majorciensis* Labeda, sp. nov., according to claim 1, wherein said microorganism has been subjected to mutagenic means such that the microorganism is genetically altered but still retains the ability to synthesize the antibiotic LL-C08078$\alpha_1$, LL-C08078$\alpha_2$, LL-C08078$\alpha_3$ or LL-C08078$\beta$.

* * * * *

UNITED STATES PATENT OFFICE
CERTIFICATE OF CORRECTION

Patent No. 4,608,343          Dated August 26, 1986

Inventor(s) David Paul Labeda et al.

It is certified that error appears in the above-identified patent and that said Letters Patent are hereby corrected as shown below:

Cover, line 1 of title, "PORE" should read --PURE--.

Column 1, line 1, "PORE" should read --PURE--.

Signed and Sealed this

Twenty-eighth Day of October, 1986

[SEAL]

Attest:

DONALD J. QUIGG

Attesting Officer          Commissioner of Patents and Trademarks